(12) United States Patent
Huang et al.

(10) Patent No.: US 11,377,511 B2
(45) Date of Patent: Jul. 5, 2022

(54) REDUCING AGENT MONOMER FOR PREPARING STYRENE-ACRYLIC EMULSION BY OXIDATION-REDUCTION REACTION AT ROOM TEMPERATURE, AND SYNTHESIS METHOD THEREOF

(71) Applicant: CHANGZHOU UNIVERSITY, Changzhou (CN)

(72) Inventors: Wenyan Huang, Changzhou (CN); Qiujie Sun, Changzhou (CN); Bibiao Jiang, Changzhou (CN); Xiaoqiang Xue, Changzhou (CN); Hongjun Yang, Changzhou (CN); Li Jiang, Changzhou (CN); Qimin Jiang, Changzhou (CN)

(73) Assignee: CHANGZHOU UNIVERSITY, Changzhou (CN)

( * ) Notice: Subject to any disclaimer, the term of this patent is extended or adjusted under 35 U.S.C. 154(b) by 0 days.

(21) Appl. No.: 17/414,980

(22) PCT Filed: Dec. 29, 2020

(86) PCT No.: PCT/CN2020/140464
§ 371 (c)(1),
(2) Date: Jun. 17, 2021

(87) PCT Pub. No.: WO2021/196775
PCT Pub. Date: Oct. 7, 2021

(65) Prior Publication Data
US 2022/0144986 A1 May 12, 2022

(30) Foreign Application Priority Data
Mar. 31, 2020 (CN) .......................... 202010242550.X

(51) Int. Cl.
*C08F 212/08* (2006.01)
*C08F 220/14* (2006.01)
*C08F 220/18* (2006.01)
*C07C 219/08* (2006.01)

(52) U.S. Cl.
CPC ...... *C08F 220/1804* (2020.02); *C07C 219/08* (2013.01); *C08F 2438/02* (2013.01)

(58) Field of Classification Search
CPC .............. C08F 220/14; C08F 220/1804; C08F 212/08; C08F 2/32
See application file for complete search history.

(56) References Cited

U.S. PATENT DOCUMENTS

| 6,369,004 B1* | 4/2002 | Klug | C08F 8/32 210/698 |
|---|---|---|---|
| 2006/0135651 A1* | 6/2006 | Nakane | C08G 18/706 427/407.1 |
| 2008/0131714 A1* | 6/2008 | Toi | C09D 143/04 428/480 |
| 2009/0087675 A1* | 4/2009 | Tonomura | C09D 133/08 427/407.1 |
| 2017/0369732 A1* | 12/2017 | Takayama | B05D 7/532 |
| 2019/0263946 A1* | 8/2019 | Huang | C08F 2/26 |

FOREIGN PATENT DOCUMENTS

| CN | 107141394 A | 9/2017 |
| CN | 111410612 A | 7/2020 |
| WO | 2017128300 A1 | 8/2017 |

OTHER PUBLICATIONS

Wei-Hung Weng, et al., A Water-Soluble Amphoteric Copolymer: Synthesis and Its Dispersion Properties on Cement Particles, Journal of Applied Polymer Science, 2010, pp. 1313-1319, vol. 118.
Konstantin Popov, et al., Synthesis and properties of novel fluorescent-tagged polyacrylate-based scale inhibitors, Journal of Applied Polymer Science, 2017, pp. 45017(1-11).

* cited by examiner

*Primary Examiner* — Karuna P Reddy
(74) *Attorney, Agent, or Firm* — Bayramoglu Law Offices LLC

(57) ABSTRACT

A reducing agent monomer for preparing a styrene-acrylic emulsion by an oxidation-reduction reaction at room temperature and a synthesis method thereof are disclosed. Maleic anhydride (MAH) and dimethylethanolamine (DMEA) are used as raw materials to synthesize the reducing agent monomer: 4-(2-(dimethylamino)ethoxy)-4-oxobut-2-enoic acid, and the synthesis method involves inexpensive easily-available raw materials, simple synthesis conditions, and easy purification. With the synthesized reducing agent monomer as a reducing agent, potassium persulfate (KPS) as an oxidizing agent, water as a dispersion medium, sodium dodecyl sulfate (SDS) as an emulsifier, and styrene, butyl acrylate (BA), and methylmethacrylate (MMA) as comonomers, free-radical microemulsion polymerization is conducted at room temperature to obtain a styrene-acrylic emulsion. In the synthesis of the styrene-acrylic emulsion, a monomer conversion rate is high, and a styrene-acrylic emulsion with a high molecular weight and a branched structure can be obtained at room temperature.

6 Claims, 4 Drawing Sheets

REDUCING AGENT MONOMER FOR PREPARING STYRENE-ACRYLIC EMULSION BY OXIDATION-REDUCTION REACTION AT ROOM TEMPERATURE, AND SYNTHESIS METHOD THEREOF

CROSS REFERENCE TO THE RELATED APPLICATIONS

This application is the national phase entry of International Application No. PCT/CN2020/140464, filed on Dec. 29, 2020, which is based upon and claims priority to Chinese Patent Application No. 202010242550.X, filed on Mar. 31, 2020, the entire contents of which are incorporated herein by reference.

TECHNICAL FIELD

The present disclosure belongs to the field of polymer synthesis, and in particular relates to a reducing agent monomer for preparing a styrene-acrylic emulsion by an oxidation-reduction reaction at room temperature, and a synthesis method thereof.

BACKGROUND

A styrene-acrylic emulsion is an emulsion obtained from the copolymerization of styrene and acrylic ester monomers. A styrene-acrylic emulsion coating prepared with a styrene-acrylic emulsion as the main film-forming substance is non-toxic and environmentally friendly, and has prominent weather resistance, color retention, and water resistance, and alkali resistance. Therefore, the styrene-acrylic emulsion has been widely used in latex paints for interior and exterior walls and other water-based coatings. Due to the special synthesis principle and film-forming mechanism, emulsion polymers are still not as good as polymers obtained by other polymerization methods in terms of the water resistance, gloss, and adhesion.

Traditional styrene-acrylic emulsions are mainly obtained by the copolymerization of styrene, butyl acrylate (BA), and a small amount of acrylic acid. The styrene-acrylic emulsions obtained by the polymerization only of three monomers show many problems, such as poor film-forming properties, high minimum film-forming temperature (MFFT), low coating strength, and poor water resistance, erosion resistance, and light resistance of a coating. In order to impart preferred properties to styrene-acrylic emulsions, a small amount of functional monomers can be introduced through blending or copolymerization to achieve the modification of styrene-acrylic emulsions. The introduction of branched polymers into an emulsion polymerization system can effectively reduce the viscosity and water absorption of an emulsion.

Emulsion polymerization is a complex polymerization affected by many factors, and the selection of an initiator has an impact on many aspects of emulsion polymerization. The use of an oxidation-reduction reaction to initiate emulsion polymerization has the advantages of low temperature, stable polymerization process, and high molecular weight. Therefore, it is of practical significance to introduce an oxidation-reduction system into a styrene-acrylic emulsion.

In existing styrene-acrylic emulsion synthesis initiated by oxidation-reduction, sodium bisulfite is generally used as a reducing agent and a peroxide is generally used as an oxidizing agent. Although active free radicals can be generated at a low temperature by reducing the activation energy for generating free radicals to initiate the polymerization reaction, a solid content in an emulsion is also slightly decreased. The introduction of branched polymers into an emulsion polymerization system can effectively reduce the viscosity and water absorption of an emulsion and increase a solid content in the emulsion. A large amount of emulsifier is often added to keep the stability of an emulsion, which will cause a paint film formed from the emulsion to have poor water resistance.

SUMMARY

The present disclosure discloses a reducing agent monomer with carboxyl, polymerizable double bond, and tertiary amino, and a synthesis method thereof. In the present disclosure, an oxidation-reduction initiation system is formed from the reducing agent monomer and a persulfate to initiate emulsion polymerization at room temperature to obtain a branched styrene-acrylic emulsion. The synthesis method of the reducing agent monomer is simple and low in cost, and leads to high product yield and purity.

The synthesis method of the reducing agent monomer of the present disclosure includes the following steps:

adding maleic anhydride (MAH) to a three-neck flask equipped with a thermometer, adding chloroform, and stirring a resulting mixture at room temperature until the MAH is completely dissolved; dissolving dimethylethanolamine (DMEA) in chloroform, and adding a resulting solution to the reaction flask all at once; reacting at room temperature for 4 h to 8 h to obtain a white suspension; adding diethyl ether, and thoroughly shaking and centrifuging a resulting mixture to obtain a white solid; and washing with diethyl ether, conducting suction filtration twice, and vacuum-drying to a constant weight to obtain a white powder.

A quantity ratio of the MAH to the DMEA may be 1:(0.5-2).

The reaction for synthesizing the reducing agent monomer may be conducted at 25° C. for 4 h to 8 h.

The reducing agent monomer obtained by the above method has a structural formula as follows:

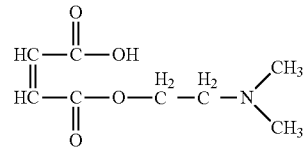

An oxidation-reduction initiation system is formed from the reducing agent monomer prepared by the above method and a persulfate to prepare a styrene-acrylic emulsion by an oxidation-reduction reaction at room temperature; and a preparation method of the styrene-acrylic emulsion may include:

adding a pH regulator, an emulsifier, the reducing agent monomer, and $H_2O$ into a 100 mL reaction flask, and stirring a resulting mixture for 3 min to 4 min to allow thorough dissolution; adding styrene, BA, and methylmethacrylate (MMA), and pre-emulsifying with stirring for about 30 min; vacuum-pumping, and adding a persulfate at an argon atmosphere; and subjecting a resulting system to free-radical microemulsion polymerization in a thermostat water bath to obtain the styrene-acrylic emulsion.

The pH regulator may be $NaHCO_3$, which is added at a mass 3% of a total mass of the monomer.

The emulsifier may be sodium dodecyl sulfate (SDS), which is added at a mass 0.5% to 1% of the total mass of the monomer.

A quantity ratio of the reducing agent monomer to the persulfate may be 1:(1-2); and the persulfate may be ammonium persulfate (APS) or potassium persulfate (KPS).

The styrene, BA, and MMA may have a quantity ratio of 1:1:0.25; and the water may be added at a mass 1.5 times a total mass of the solids.

The polymerization may be conducted at 25° C. for 8 h to 12 h.

Advantages of the present disclosure: The synthesis method of the reducing agent monomer provided in the present disclosure is simple and low in cost, and leads to high product yield and purity. The obtained reducing agent monomer with polymerizable double bond, carboxyl, and tertiary amino and a persulfate can form an oxidation-reduction initiation system to initiate styrene-acrylic emulsion polymerization to obtain a branched styrene-acrylic emulsion with terminal carboxyl. With the polymerization process, a branched styrene-acrylic emulsion with a high molecular weight can be obtained at room temperature.

Compared with the prior art, the present disclosure has the following beneficial technical effects.

1. The synthesis method of the reducing agent monomer provided in the present disclosure involves cheap and easily-available raw materials, simple synthesis conditions, and easy purification. The entire reaction system is simple and stable and involves mild conditions, no temperature control, simple and easy operations, little impact on the environment, and low energy consumption, which is suitable for industrial large-scale production.

2. The synthesis method of the styrene-acrylic emulsion provided in the present disclosure involves mild reaction conditions and high monomer conversion rate, and a styrene-acrylic emulsion with a high molecular weight and a branched structure can be obtained at room temperature. The obtained styrene-acrylic resin has a high molecular weight, and the molecular weight and branching degree of the styrene-acrylic resin can be adjusted in a wide range.

DETAILED DESCRIPTION OF THE EMBODIMENTS

The technical features of the present disclosure are further illustrated with the following examples, but a protection scope of the present disclosure is not limited to the following examples.

Example 1

Synthesis of a Reducing Agent Monomer

Figure 1:
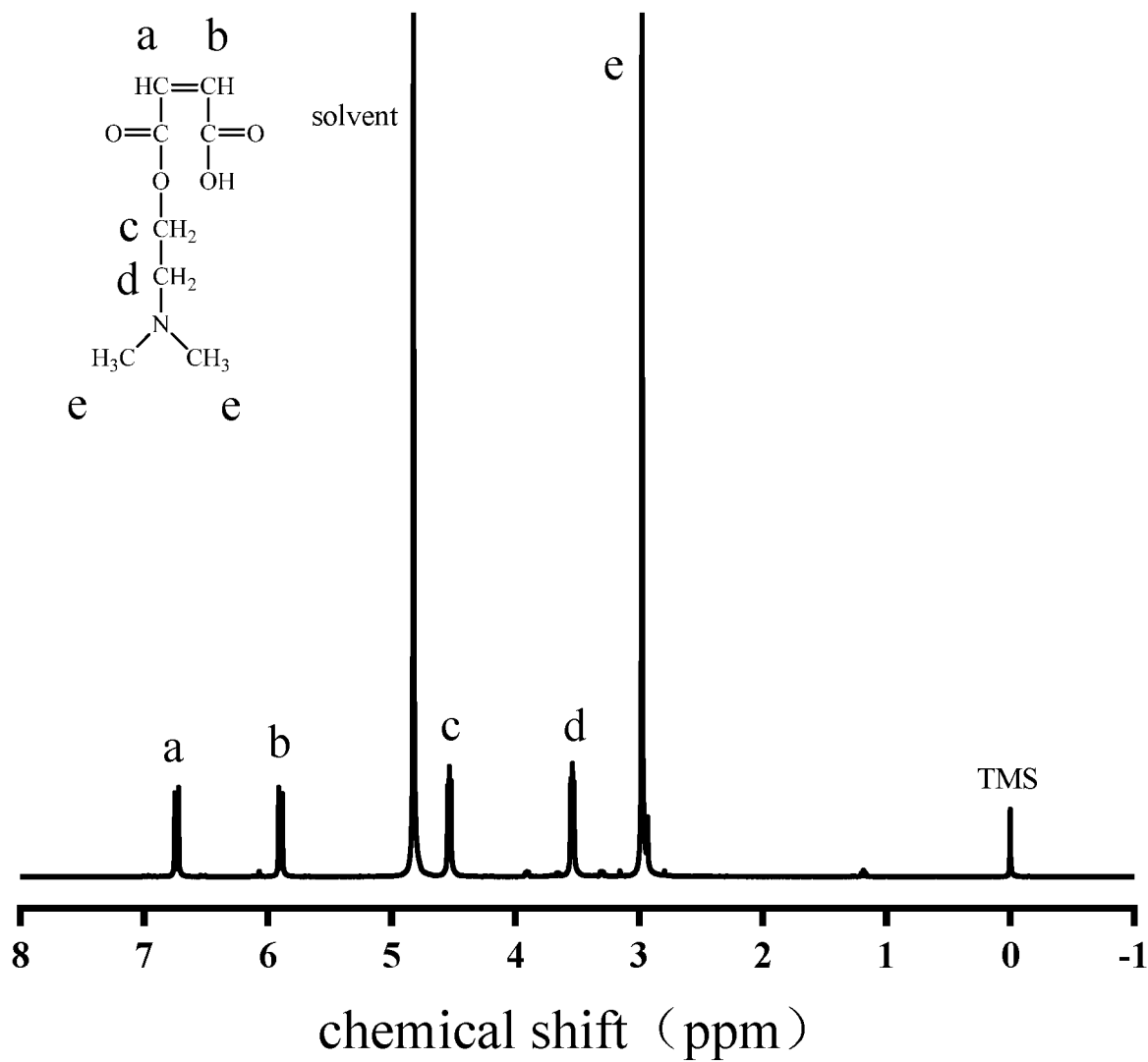
FIG. 1 is a nuclear magnetic resonance (NMR) spectrum of the reducing agent monomer: 4-(2-(dimethylamino)ethoxy)-4-oxobut-2-enoic acid.

MAH (4.9 g, 0.05 mol) was added to a three-neck flask equipped with a thermometer, 30 mL of chloroform was added, and a resulting mixture was stirred at room temperature until the MAH was completely dissolved; DMEA (4.5 g, 0.05 mol) was dissolved in 10 mL of chloroform, and a resulting solution was added to the reaction flask all at once; a resulting system reacted at room temperature for 5 h to obtain a white suspension; 40 mL of diethyl ether was added, and a resulting mixture was thoroughly shaken and centrifuged to obtain a white solid; and the white solid was washed with 40 mL of diethyl ether, then suction filtration was conducted twice, and a resulting filter cake was vacuum-dried to a constant weight to obtain a white powder, with a total yield of 94.5%. An NMR spectrum of the product is shown in FIG. 1 of the specification.

Example 2

Synthesis of a Reducing Agent Monomer

MAH (4.9 g, 0.05 mol) was added to a three-neck flask equipped with a thermometer, 30 mL of chloroform was added, and a resulting mixture was stirred at room temperature until the MAH was completely dissolved; DMEA (2.3 g, 0.025 mol) was dissolved in 8 mL of chloroform, and a resulting solution was added to the reaction flask all at once; a resulting system reacted at room temperature for 4 h to obtain a white suspension; 40 mL of diethyl ether was added, and a resulting mixture was thoroughly shaken and centrifuged to obtain a white solid; and the white solid was washed with 40 mL of diethyl ether, then suction filtration was conducted twice, and a resulting filter cake was vacuum-dried to a constant weight to obtain a white powder, with a total yield of 65.7%.

Example 3

Synthesis of a Reducing Agent Monomer

MAH (4.9 g, 0.05 mol) was added to a three-neck flask equipped with a thermometer, 30 mL of chloroform was added, and a resulting mixture was stirred at room temperature until the MAH was completely dissolved; DMEA (9.0 g, 0.10 mol) was dissolved in 20 mL of chloroform, and a resulting solution was added to the reaction flask all at once; a resulting system reacted at room temperature for 8 h to obtain a white suspension; 40 mL of diethyl ether was added, and a resulting mixture was thoroughly shaken and centrifuged to obtain a white solid; and the white solid was washed with 40 mL of diethyl ether, then suction filtration was conducted twice, and a resulting filter cake was vacuum-dried to a constant weight to obtain a white powder, with a total yield of 57.7%.

Example 4

Figure 2:
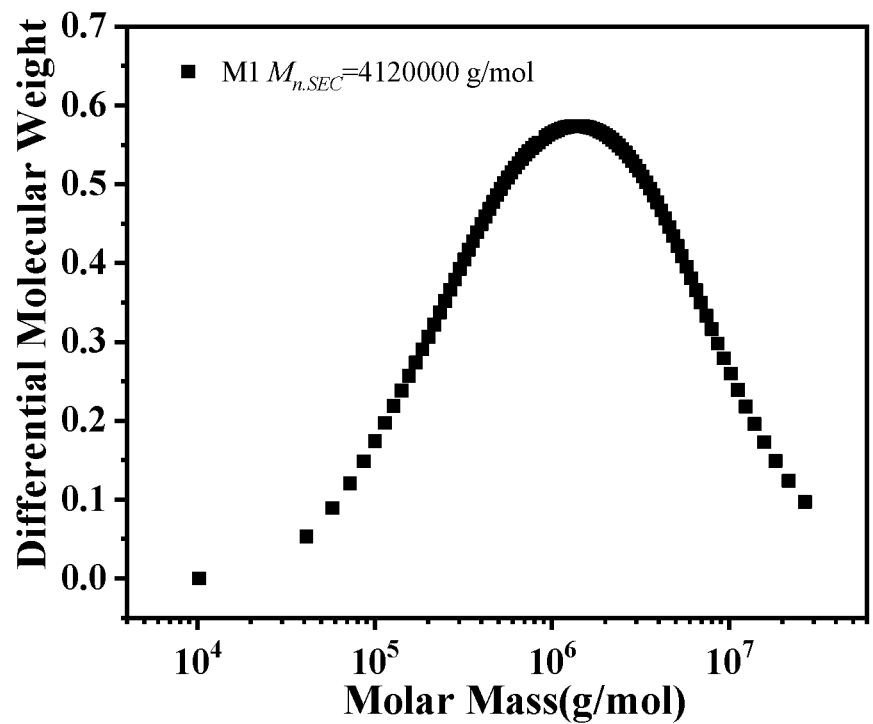
FIG. 2 shows a differential molecular weight distribution curve of the polymer obtained in Example 4.
Figure 5:
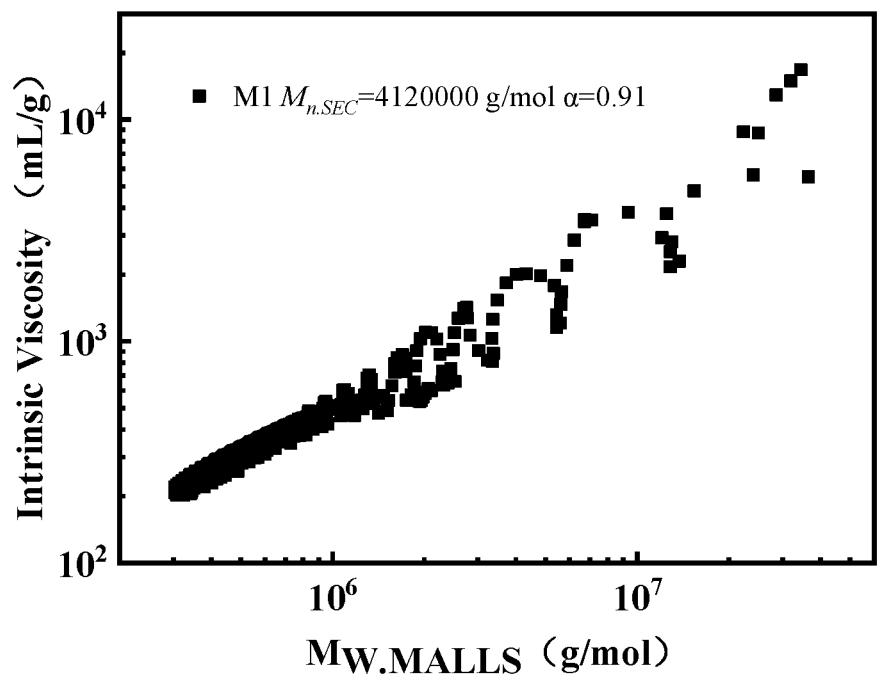
FIG. 5 shows a Mark-Houwink curve of the polymer obtained in Example 4.

Emulsion Polymerization NaHCO$_3$ (0.0772 g, 3 wt % of total monomer), SDS (0.0117 g, 0.5 wt % of total monomer), the reducing agent monomer obtained in Example 1 (0.0187 g, 0.0001 mol), and H$_2$O (4.2132 g, 60 wt % of emulsion) were weighed and added into a 50 mL reaction flask, and a resulting mixture was stirred for 3 min to 4 min to allow thorough dissolution; then styrene (1.0415 g, 0.01 mol), BA (1.2817 g, 0.01 mol), and MMA (0.2503 g, 0.0025 mol) were added, and pre-emulsification was conducted with stirring for about 30 min; vacuum-pumping was conducted, and APS (0.0228 g, 0.0001 mol) was added at an argon atmosphere; and a resulting system reacted for 8 h in a 25° C. thermostat water bath to obtain the styrene-acrylic emulsion. As determined, a styrene conversion rate was 94%, a BA conversion rate was 94%, an MMA conversion rate was 96%, and a solid content was 59%. Then the emulsion was dropped into absolute methanol for demulsification, a resulting mixture was subjected to suction filtration with a Buchner funnel, and a resulting filter cake was dissolved in THF; and the absolute methanol precipitation was repeated three times to obtain a polymer M1. The polymer was analyzed by three-detection gel permeation chromatography (TG-GPC), and results were as follows: $M_{n,SEC}$=4,120,000 g/mol, $M_{w,SEC}$=30,090,000 g/mol, PDI=7.3, Mark-Houwink index α=0.568, and average branching factor g'=0.91. A differential molecular weight distribution curve of the obtained polymer M1 is shown in FIG. 2 of the specification; and a Mark-Houwink curve of the polymer M1 is shown in FIG. 5 of the specification.

Example 5

Figure 3:
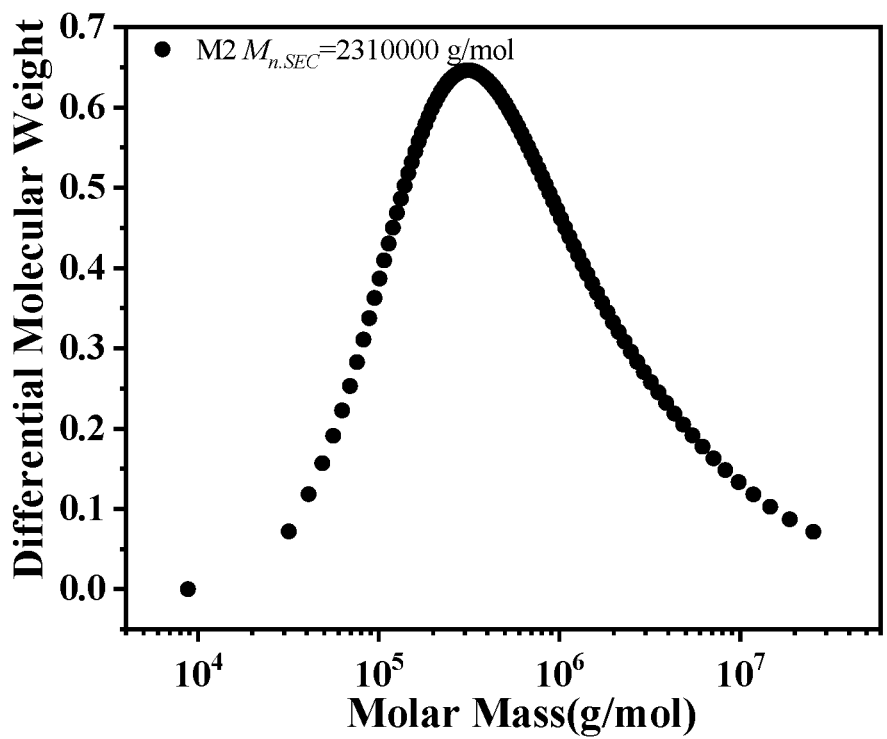
FIG. 3 shows a differential molecular weight distribution curve of the polymer obtained in Example 5.
Figure 6:
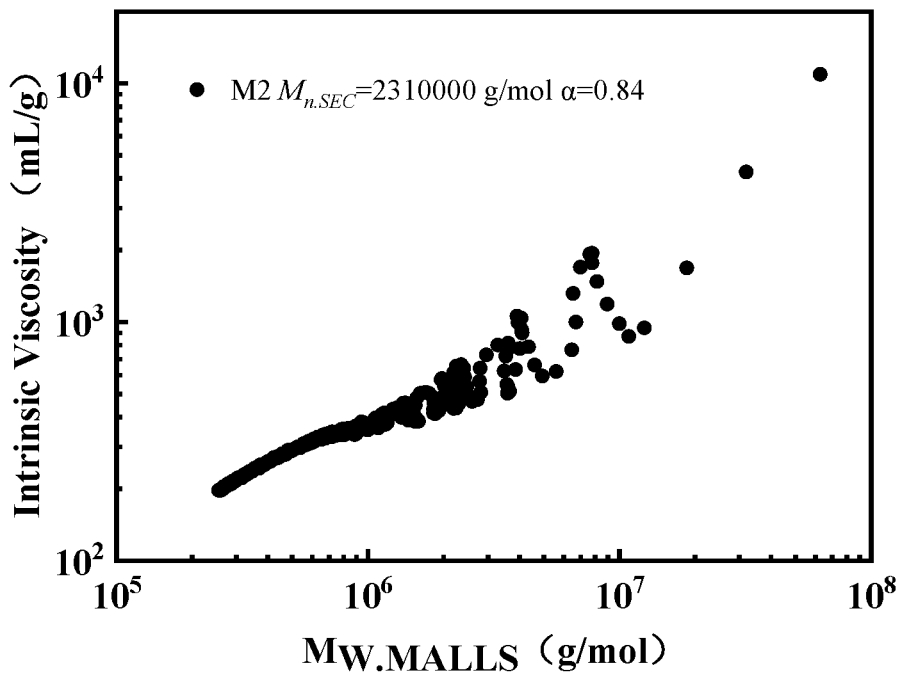
FIG. 6 shows a Mark-Houwink curve of the polymer obtained in Example 5.

Emulsion Polymerization $NaHCO_3$ (0.0772 g, 3 wt % of total monomer), SDS (0.0119 g, 0.5 wt % of total monomer), the reducing agent monomer obtained in Example 1 (0.0561 g, 0.0003 mol), and $H_2O$ (4.3377 g, 60 wt % of emulsion) were weighed and added into a 50 mL reaction flask, and a resulting mixture was stirred for 3 min to 4 min to allow thorough dissolution; then styrene (1.0415 g, 0.01 mol), BA (1.2817 g, 0.01 mol), and MMA (0.2503 g, 0.0025 mol) were added, and pre-emulsification was conducted with stirring for about 30 min; vacuum-pumping was conducted, and APS (0.0684 g, 0.0003 mol) was added at an argon atmosphere; and a resulting system reacted for 8 h in a 25° C. thermostat water bath to obtain the styrene-acrylic emulsion. As determined, a styrene conversion rate was 99%, a BA conversion rate was 99%, an MMA conversion rate was 92%, and a solid content was 59%. Then the emulsion was dropped into absolute methanol for demulsification, a resulting mixture was subjected to suction filtration with a Buchner funnel, and a resulting filter cake was dissolved in THF; and the absolute methanol precipitation was repeated three times to obtain a polymer M2. The polymer was analyzed by TG-GPC, and results were as follows: $M_{n,SEC}$=2,310,000 g/mol, $M_{w,SEC}$=17,800,000 g/mol, PDI=7.8, Mark-Houwink index α=0.521, and average branching factor g'=0.84. A differential molecular weight distribution curve of the obtained polymer M2 is shown in FIG. 3 of the specification; and a Mark-Houwink curve of the polymer M2 is shown in FIG. 6 of the specification.

Example 6

Figure 4:
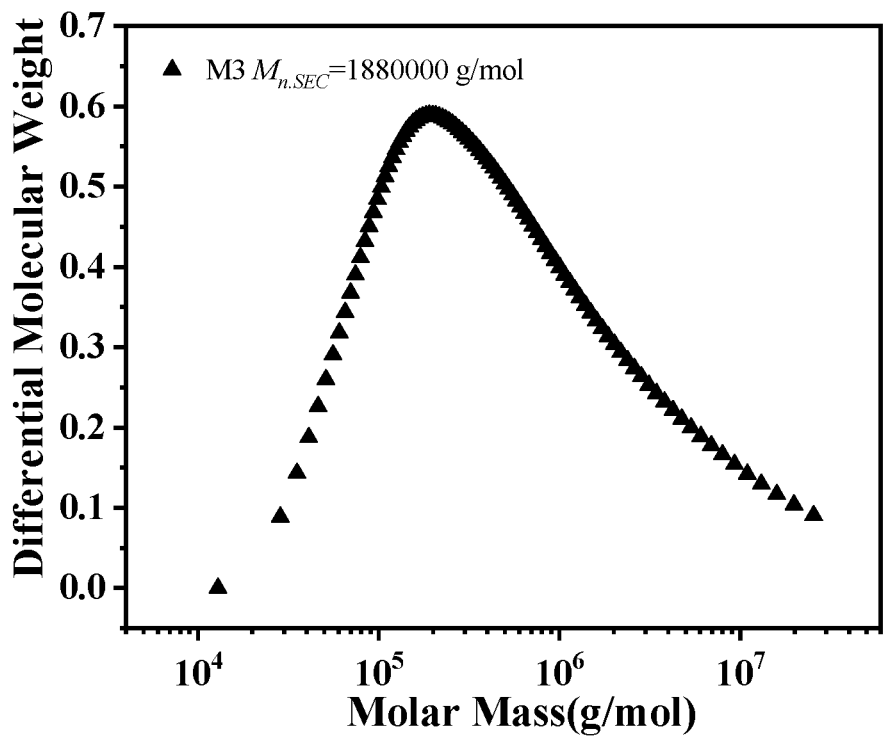
FIG. 4 shows a differential molecular weight distribution curve of the polymer obtained in Example 6.
Figure 7:
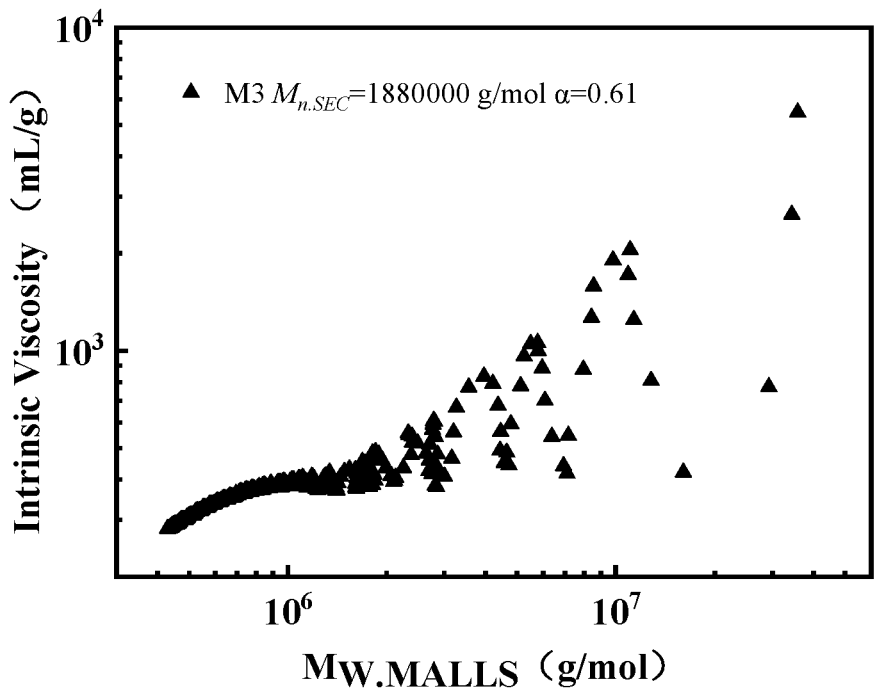
FIG. 7 shows a Mark-Houwink curve of the polymer obtained in Example 6.

Emulsion Polymerization $NaHCO_3$ (0.0772 g, 3 wt % of total monomer), SDS (0.0121 g, 0.5 wt % of total monomer), the reducing agent monomer obtained in Example 1 (0.187 g, 0.001 mol), and $H_2O$ (4.7734 g, 60 wt % of emulsion) were weighed and added into a 50 mL reaction flask, and a resulting mixture was stirred for 3 min to 4 min to allow thorough dissolution; then styrene (1.0415 g, 0.01 mol), BA (1.2817 g, 0.01 mol), and MMA (0.2503 g, 0.0025 mol) were added, and pre-emulsification was conducted with stirring for about 30 min; vacuum-pumping was conducted, and APS (0.228 g, 0.001 mol) was added at an argon atmosphere; and a resulting system reacted for 8 h in a 25° C. thermostat water bath to obtain the styrene-acrylic emulsion. As determined, a styrene conversion rate was 100%, a BA conversion rate was 97%, an MMA conversion rate was 96%, and a solid content was 59%. Then the emulsion was dropped into absolute methanol for demulsification, a resulting mixture was subjected to suction filtration with a Buchner funnel, and a resulting filter cake was dissolved in THF; and the absolute methanol precipitation was repeated three times to obtain a polymer M3. The polymer was analyzed by TG-GPC, and results were as follows: $M_{n,SEC}$=1,880,000 g/mol, $M_{w,SEC}$=18,900,000 g/mol, PDI=10.0, Mark-Houwink index α=0.408, and average branching factor g'=0.65. A differential molecular weight distribution curve of the obtained polymer M3 is shown in FIG. 4 of the specification; and a Mark-Houwink curve of the polymer M3 is shown in FIG. 7 of the specification.

Example 7

Emulsion Polymerization $NaHCO_3$ (0.0768 g, 3 wt % of total monomer), SDS (0.0023 g, 0.1 wt % of total monomer), the reducing agent monomer obtained in Example 1 (0.187 g, 0.001 mol), and $H_2O$ (4.7734 g, 60 wt % of emulsion) were weighed and added into a 50 mL reaction flask, and a resulting mixture was stirred for 3 min to 4 min to allow thorough dissolution; then styrene (1.0415 g, 0.01 mol), BA (1.2817 g, 0.01 mol), and MMA (0.2503 g, 0.0025 mol) were added, and pre-emulsification was conducted with stirring for about 30 min; vacuum-pumping was conducted, and KPS (0.5411 g, 0.002 mol) was added at an argon atmosphere; and a resulting system reacted for 12 h in a 25° C. thermostat water bath to obtain the styrene-acrylic emulsion. As determined, a styrene conversion rate was 92%, a BA conversion rate was 86%, an MMA conversion rate was 90%, and a solid content was 57%. Then the emulsion was dropped into absolute methanol for demulsification, a resulting mixture was subjected to suction filtration with a Buchner funnel, and a resulting filter cake was dissolved in THF; and the absolute methanol precipitation was repeated three times to obtain a polymer. The polymer was analyzed by TG-GPC, and results were as follows: $M_{n,SEC}$=2,070,000 g/mol, $M_{w,SEC}$=22,200,000 g/mol, PDI=6.3, Mark-Houwink index α=0.608, and average branching factor g'=0.77.

Comparative Example 1

$NaHCO_3$ (0.0770 g, 3 wt % of total monomer), SDS (0.0021 g, 0.1 wt % of total monomer), and $H_2O$ (7.3060 g, 60 wt % of emulsion) were weighed and added into a 50 mL reaction flask, and a resulting mixture was stirred for 3 min to 4 min to allow thorough dissolution; then styrene (1.0420 g, 0.01 mol), BA (1.2812 g, 0.01 mol), and MMA (0.2510 g, 0.0025 mol) were added, and pre-emulsification was conducted with stirring for about 30 min; vacuum-pumping was conducted, and an oxidizing agent of KPS (0.5413 g, 0.002 mol) and a reducing agent of dimethylaminoethyl methacrylate (DMAEMA) (0.3145 g, 0.002 mol) were added at an argon atmosphere; and a resulting system was placed in a 25° C. thermostat water bath, and no reaction occurred in the system.

Comparative Example 2

$NaHCO_3$ (0.0770 g, 3 wt % of total monomer), SDS (0.1040 g, 5 wt % of total monomer), and $H_2O$ (7.3060 g, 60 wt % of emulsion) were weighed and added into a 50 mL reaction flask, and a resulting mixture was stirred for 3 min to 4 min to allow thorough dissolution; then styrene (1.0420 g, 0.01 mol), BA (1.2812 g, 0.01 mol), and MMA (0.2510 g, 0.0025 mol) were added, and pre-emulsification was conducted with stirring for about 30 min; vacuum-pumping was conducted, and an oxidizing agent of KPS (0.5413 g, 0.002 mol) and a reducing agent of DMAEMA (0.3145 g, 0.002 mol) were added at an argon atmosphere; a resulting system reacted for 12 h in a 25° C. thermostat water bath, and the system underwent agglomeration; and demulsification was conducted. As determined, a styrene conversion rate was 63%, a BA conversion rate was 55%, an MMA conversion rate was 60%, and a solid content was 30%. Then the emulsion was dropped into absolute methanol for demulsification, a resulting mixture was subjected to suction filtration with a Buchner funnel, and a resulting filter cake was dissolved in THF; and the absolute methanol precipitation was repeated three times to obtain a polymer. The polymer was analyzed by TG-GPC, and results were as follows: $M_{n,SEC}$=207,800 g/mol, $M_{w,SEC}$=898,000 g/mol, PDI=4.3, Mark-Houwink index $\alpha$=0.7173, and average branching factor g'=0.98.

Comparative Example 3

$NaHCO_3$ (0.0768 g, 3 wt % of total monomer), SDS (0.1032 g, 5 wt % of total monomer), and $H_2O$ (7.3066 g, 60 wt % of emulsion) were weighed and added into a 50 mL reaction flask, and a resulting mixture was stirred for 3 min to 4 min to allow thorough dissolution; then styrene (1.0415 g, 0.01 mol), BA (1.2817 g, 0.01 mol), and MMA (0.2503 g, 0.0025 mol) were added, and pre-emulsification was conducted with stirring for about 30 min; vacuum-pumping was conducted, and an oxidizing agent of KPS (0.5411 g, 0.002 mol) and a reducing agent of sodium bisulfite (0.2609 g, 0.0025 mol) were added at an argon atmosphere; and a resulting system reacted for 24 h in a 25° C. thermostat water bath to obtain a styrene-acrylic emulsion. As determined, a styrene conversion rate was 89%, a BA conversion rate was 85%, an MMA conversion rate was 86%, and a solid content was 38%. Then the emulsion was dropped into absolute methanol for demulsification, a resulting mixture was subjected to suction filtration with a Buchner funnel, and a resulting filter cake was dissolved in THF; and the absolute methanol precipitation was repeated three times to obtain a polymer. The polymer was analyzed by TG-GPC, and results were as follows: $M_{n,SEC}$=306,000 g/mol, $M_{w,SEC}$=2,110,000 g/mol, PDI=6.9, Mark-Houwink index $\alpha$=0.7896, and average branching factor g'=1.

What is claimed is:

1. A method for preparing a styrene-acrylic emulsion by an oxidation-reduction reaction at room temperature using an oxidation-reduction initiation system, wherein
the oxidation-reduction initiation system is formed from a reducing agent monomer and a persulfate, and the reducing agent monomer is 4-(2-(dimethylamino) ethoxy)-4-oxobut-2-enoic acid synthesized using maleic anhydride (MAH) and dimethylethanolamine (DMEA) as raw materials;
the method comprises:
adding a pH regulator, an emulsifier, the reducing agent monomer, and a dispersion medium into a reaction flask to obtain a mixture, and stirring said mixture for 3 min to 4 min to allow a thorough dissolution to obtain a mixed solution, wherein the dispersion medium is water ($H_2O$);
adding monomers into the mixed solution for pre-emulsification under stirring for 30 min to obtain a pre-emulsified product, wherein the monomers comprise styrene, butyl acrylate (BA), and methyl methacrylate (MMA);
vacuum-pumping, and adding the persulfate to the pre-emulsified product in an argon atmosphere to obtain a resulting system; and
subjecting the resulting system to a free-radical microemulsion polymerization in a thermostat water bath to obtain the styrene-acrylic emulsion.

2. The method according to claim 1, wherein a mass quantity ratio of the reducing agent monomer to persulfate is 1:(1-2); and the persulfate is ammonium persulfate (APS) or potassium persulfate (KPS).

3. The method according to claim 1, wherein the water is added at a mass of 1.5 times total mass of solids; and the styrene, the BA, and the MMA have a mass ratio of 1:1:0.25.

4. The method according to claim 1, wherein the emulsifier is sodium dodecyl sulfate (SDS), and the SDS is added at a mass 0.5% to 1% based on a total mass of the reducing agent monomer and the monomers styrene, butyl acrylate (BA), and methyl methacrylate (MMA).

5. The method according to claim 1, wherein the free-radical microemulsion polymerization is conducted at 25° C. for 8 h to 12 h.

6. The method according to claim 1, wherein the pH regulator is $NaHCO_3$, and the $NaHCO_3$ is added at a mass of 3% based on a total mass of the reducing agent monomer and the monomers styrene, butyl acrylate (BA), and methyl methacrylate (MMA).

* * * * *